(12) United States Patent
Remskar et al.

(10) Patent No.: US 9,151,724 B2
(45) Date of Patent: Oct. 6, 2015

(54) METHOD AND CAPACITIVE SENSOR FOR COUNTING AEROSOL NANOPARTICLES

(75) Inventors: Maja Remskar, Medvode (SI); Ivan Iskra, Ilirska Bistrica (SI); Marko Virsek, Grosuplje (SI); Mark Plesko, Komen (SI); Damjan Golob, Smartno pri Litiji (SI)

(73) Assignee: Institute Jozef Stefan, Ljubljana (SI)

( * ) Notice: Subject to any disclaimer, the term of this patent is extended or adjusted under 35 U.S.C. 154(b) by 109 days.

(21) Appl. No.: 13/126,090

(22) PCT Filed: Oct. 8, 2009

(86) PCT No.: PCT/SI2009/000045
§ 371 (c)(1),
(2), (4) Date: Jul. 11, 2011

(87) PCT Pub. No.: WO2010/050904
PCT Pub. Date: May 6, 2010

(65) Prior Publication Data
US 2011/0259082 A1 Oct. 27, 2011

(30) Foreign Application Priority Data
Oct. 27, 2008 (SI) .................. P-200800256

(51) Int. Cl.
*G01N 27/22* (2006.01)
*G01N 15/06* (2006.01)
*G01N 15/00* (2006.01)

(52) U.S. Cl.
CPC .......... *G01N 27/221* (2013.01); *G01N 15/0656* (2013.01); *G01N 2015/0038* (2013.01)

(58) Field of Classification Search
CPC .................. G01N 2015/0038; G01N 27/221; G01N 15/0656

USPC .............................................. 73/28.01, 28.02
See application file for complete search history.

(56) References Cited

U.S. PATENT DOCUMENTS

| | | |
|---|---|---|
| 4,790,650 A | 12/1988 | Keady |
| 5,118,959 A | 6/1992 | Caldow et al. |

(Continued)

FOREIGN PATENT DOCUMENTS

| | | |
|---|---|---|
| DE | 102004041620 A1 | 3/2006 |
| WO | 0131312 A2 | 5/2001 |
| WO | 2008074559 A1 | 6/2008 |

OTHER PUBLICATIONS

K.M. Adams, "Real-time in situ measurements of atmospheric optical absorption in the visible via photoaccoustic spectroscopy," copyright 1988, 1: Evaluation of photoacoustic cells, Applied Optics, vol. 27, No. 19, pp. 4052-4056.
Dekati® ELPI™ Electrical Low Pressure Impactor, copyright 2010, Dekati Ltd., Finland.
International Search Report mailed on Feb. 12, 2010 in PCT/EP2009/000045.

(Continued)

*Primary Examiner* — John Fitzgerald
*Assistant Examiner* — David Z Huang
(74) *Attorney, Agent, or Firm* — MacCord Mason PLLC (57) ABSTRACT

The invention refers to a method and capacitive sensor for counting aerosol nanoparticles in an electric way. Aerosol particles, onto which a fluid was applied in an earlier process by known methods, change the capacitance of the dielectric of the capacitor when entering its field, which causes an electric signal. The method provides for detection of aerosol particles in a wide scope of their presence in the air and is not specific for any shape or chemical composition of nanoparticles.

5 Claims, 6 Drawing Sheets

(56) References Cited

U.S. PATENT DOCUMENTS

| | | | |
|---|---|---|---|
| 5,143,696 | A | 9/1992 | Haas et al. |
| 5,668,309 | A | 9/1997 | Codina et al. |
| 5,870,190 | A | 2/1999 | Unger |
| 6,091,494 | A | 7/2000 | Kreikebaum |
| 6,365,856 | B1 * | 4/2002 | Whitelaw .................. 209/127.1 |
| 6,450,026 | B1 | 9/2002 | Desarnaud |
| 6,750,449 | B2 | 6/2004 | Marcus |
| 6,936,828 | B2 | 8/2005 | Saccomanno |
| 7,119,331 | B2 | 10/2006 | Chang et al. |
| 7,298,486 | B2 | 11/2007 | Wang et al. |
| 7,712,348 | B2 * | 5/2010 | Luebbert et al. ............. 73/29.04 |
| 7,864,063 | B2 * | 1/2011 | Rienecker .................... 340/604 |
| 2004/0012772 | A1 | 1/2004 | Ahn et al. |
| 2004/0012912 | A1 | 1/2004 | Rombach |
| 2006/0146327 | A1 | 7/2006 | Wang et al. |
| 2008/0034839 | A1 | 2/2008 | Ante et al. |
| 2009/0134026 | A1 | 5/2009 | Lagenbacher |
| 2010/0129285 | A1 | 5/2010 | Mrzel et al. |

OTHER PUBLICATIONS

A. Keller, M. Ruegg, M. Forster, M. Loepfe, R. Pleisch, P. Nebiker, H. Burtscher, "Open photoacoustic sensor as smoke detector," copyright 2005, Sensors and Actuators B, vol. 104, pp. 1-7.

J. Keskinen, K. Pietarinen, and M. Lehtimaki, "Electrical low pressure impactor," copyright 1992, Journal of Aerosol Science, vol. 23, No. 4, pp. 353-360.

W. Luther et al., "Technological Analysis: Industrial application of nanomaterials—chances and risks," copyright 2004, Future technologies, No. 54, Dusseldorf: Future Technologies Division of VDI Technologiezentrum.

Remskar et al., U.S. Appl. No. 12/528,162, filed Aug. 21, 2009.

A. Virtanen, M. Marjamaki, J. Ristimaki, J. Keskinen, "Fine particle losses in electrical low-pressure impactor," copyright 2001, Aerosol Science, vol. 32, pp. 389-401.

Written Opinion mailed on Feb. 12, 2010 in PCT/EP2009/000045.

* cited by examiner

METHOD AND CAPACITIVE SENSOR FOR COUNTING AEROSOL NANOPARTICLES

This application is a national stage application under 35 U.S.C. 371 of International Application No.: PCT/SI2009/000045 filed 8 Oct. 2009, which claims priority to Slovenian Application No.: P-200800256 filed 27 Oct. 2008, the disclosures of which are expressly incorporated herein by reference.

FIELD OF INVENTION

The subject of the present invention is a method and capacitive sensor for counting nanoparticles in the air, i.e. aerosol nanoparticles. The invention belongs to the field of aerosol detection.

Technical Problem

Emission of nanoparticles to the environment presents a serious risk to human health since it has an important effect on the quality of life, life expectancy and work conditions. Work environments, in which a man spends much time is loaded with produced, i.e. engineered nanoparticles. Both work and general environment are full of high concentrations of undeliberately produced aerosol nanoparticles that are produced in industrial processes, like milling, welding, grinding, cutting etc. and also those resulting from the combustion of fossil fuels, like diesel engines and biomass.

Equipment for detecting aerosol nanoparticles and measurement of their number as a function of their size is a must in various stages of production, use and recycling process of materials containing nanoparticles as well as for the supervision and protection of general environment. Several devices of this type are already available on the market, however, they are technologically very complex and consequently expensive. The devices are relatively large, heavy and consume plenty of energy for operation and call for frequent servicing. A yet more considerable technical problem is the invention of a method for counting nanoparticles that would be applicable in a large scope of number density of nanoparticles and would be independent of air humidity. The goal of this patent is the invention of a method for counting aerosol nanoparticles that provides for the manufacturing of both portable nanoparticle detectors for personal protection and more affordable stationary detectors causing low operating and maintenance costs. A detector must thus have a good self-cleaning component, low consumption of energy and fluid for coating nanoparticles and a possibility of supply from a battery source.

PRIOR ART

Several different methods for detecting nanoparticles in the air are known. Adequate metric for exposure to nanoparticles can be number concentration, distribution of particles by size, specific surface or shape. A technology that would combine all these metrics simultaneously is not yet available, especially if we talk about routine measurement of exposure to nanoparticles of an individual (W. Luthar et al., *Industrial application of nanomaterials—chances and risks: technology analysis*, (Future technologies, No. 54), Düsseldorf: Future Technologies Division of VDI Technologiezentrum, 2004).

Known methods providing for the measurement of number concentration of aerosol nanoparticles are as follows:

1. CPC (Condensation Particle Counter) that counts nanoparticles, on which a fluid, usually butanole or water, condenses. Particles thus coated are counted by optical methods (the method is described in detail in PCT/US00/41612).

2. SMPS (Scanning Mobility Particle Sizer). In this method nanoparticles are first sorted by size by using a DMA—Differential Mobility Analyser operating by the principle of distortion of electrically loaded particles within an electric field. Thereafter individual fractions are lead to a condensation chamber of the CPC. The method is described in more detail in U.S. Pat. Nos. 4,790,650 and 5,118,959.

3. BLPI (Berner Low Pressure Impactor). A Berner type impactor counts particles based on weighing. The method comprises several consecutive chambers, in which air flow with nanoparticles is directed through pores that get smaller and smaller to a narrow area between two chambers, where the air flow recurves and the particles exceeding a certain size cannot follow the air flow due to inertion and hit the ground, where they are weighed. The method is described in A. Berner, *Staub-Reinhaltung der Luft.* 36: 385-390, 417-419 (1976).

4. ELPI (Electrical Low Pressure Impactor) first charges the particles selected by size with a Berner type impactor and then counts them based on the measurement of the electric charge. The method is described in detail in J. Keskinen et al, Journal of Aerosol Science, vol. 23, p. 353 (1992) and in A. Virtanen et al., Aerosol Science, vol. 32, p. 389 (2001).

Aerosol nanoparticle counters used by the above three methods are relatively large and unhandy. The ELPI detector can count particles above 7 nm, wherein the SMPS makes it possible to detect particles having diameters exceeding 3 nm. Although the condensation particle counter (CPC) is much smaller, it is still not suitable for personal use.

A methodology of counting aerosol nanoparticles in their original size and without a radioactive or fluorescent marker has not yet been developed, except for some specific purposes. In these cases scattering of light was used as disclosed in U.S. Pat. No. 6,936,828 B2, U.S. Pat. No. 6,750,449 B2 and U.S. Pat. No. 6,091,494 A and laser induced fluorescence for detecting an aerosol particle as disclosed in the U.S. Pat. No. 7,119,331 B2. A method of flowing through is also used: the size of a nanoparticle is deducted from a comparison between voltage pulses on a detector caused by a nanoparticle as disclosed in U.S. Pat. No. 5,870,190. The methodology of counting coated nanoparticles with optical and opto-acustic methods is known and described in the U.S. Pat. No. 7,298,486 B2, in K. M. Adams, Applied Optics vol. 27, p. 4052 (1988) and in A. Keller, M. Rüegg, M. Forster, M. Loepfe, R. Pleisch, P. Nebiker, H. Burtscher, Sensors and Actuators B vol. 104.1 (2005). It only conditionally counts to those that provide for measurement of distribution of aerosol nanoparticles by size. The light, with which nanoparticle-containing gas is illuminated, gets absorbed in these particles and they consequently get heated. The heat is transferred to the particle environment and causes changes in local pressure in compliance with modulation of light frequency. Changes in pressure are measured by a sensitive microphone. Disadvantages of said method are great sensitivity to changes in temperature, composition of carrier gas and changes in the speed of sound linked thereto.

A method for the counting of nanoparticles that would be based on the measurement of change in the capacitance of a capacitor has not yet been described.

GOAL AND PURPOSE OF THE INVENTION

The goal of the present invention is a method and a capacitive sensor for counting aerosol nanoparticles. The method should be adequate for the measurement in a wide scope of their presence in the air and should not be specific only for a certain shape or chemical composition of nanoparticles and should further allow a design of a sensor for the production of a relatively light-weight and portable detector of nanoparticles in the air.

The task of the invention is solved as follows: nanoparticles, on which a fluid had condensed in an earlier process, change the capacitance of the capacitor after having entered the space of the dielectric capacitor, said capacitor presenting a capacitive sensor of the invention. This method provides for detection of aerosol nanoparticles in a wide scope of their presence in the air. Moreover, the method is not specific for a certain shape or chemical composition of nanoparticles. The task of the invention is solved by independent patent claims.

DESCRIPTION OF THE INVENTION

The invention will be explained by way of an embodiment in the form of a device for counting aerosol nanoparticles, by way of an experiment and by way of figures showing in:

FIG. 1: a) a schematic view of a capacitive sensor, b) a side view of the capacitive sensor, c) two rake-shaped electrodes FIG. 2: an electrode 102 of the capacitive sensor; a) optical image; b) scanning electron microscope (SEM) image taken with a high-resolution microscope for field emission (FE-SEM, Supra 35 VP, Carl Zeiss)

Figure 3:
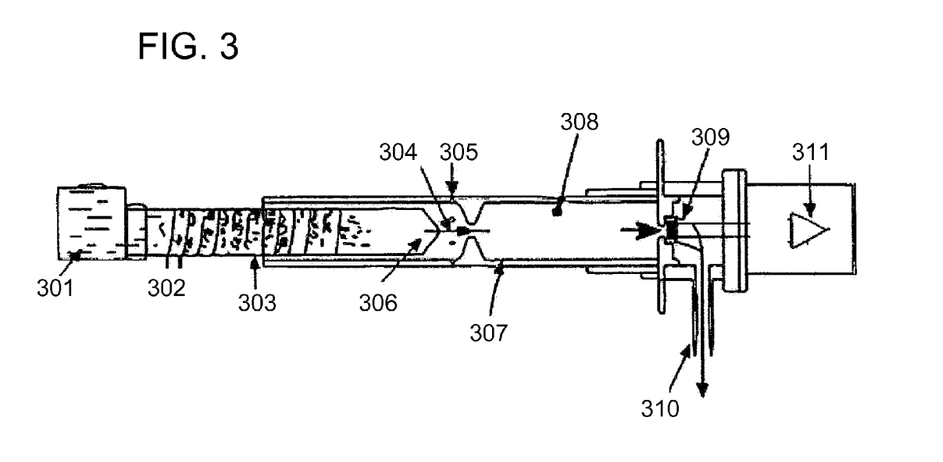
FIG. 3: a schematic view of a device for counting aerosol nanoparticles with marked position of the capacitive sensor for counting nanoparticles.

A device for counting aerosol nanoparticles as shown in FIG. 3 consists of a known device or known filters for the separation of aerosol nanoparticles by size, of a known device for coating nanoparticles, a capacitive sensor of the invention and suitable electronics for capturing and processing signals from the sensor.

Figure 1A:
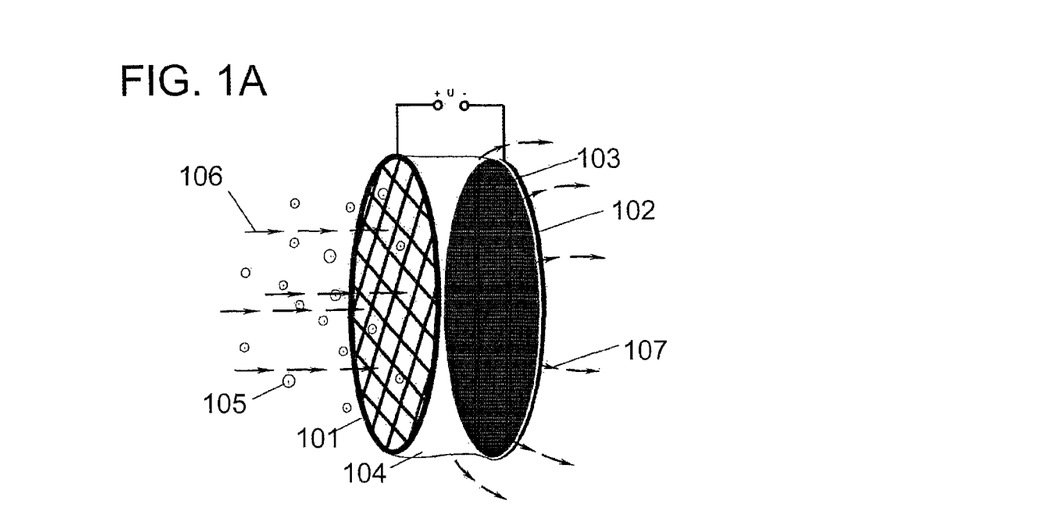
Figure 1B:
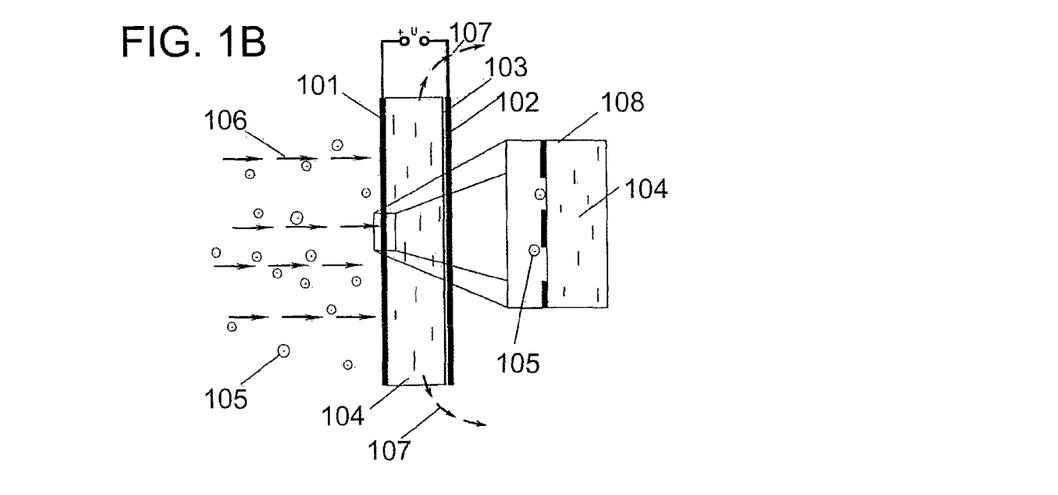

A capacitive sensor of the invention and as shown in the embodiment in FIGS. 1a and 1b is represented by two electrodes connected to a source of direct voltage with a capacitance meter. A first electrode 101 is manufactured in a way to allow outflow of fluid coated nanoparticles 105 towards direction 106 to a space 104 of a dielectric. The electrode 101 is preferably perforated and manufactured as a mesh with the size of pores ranging from a few tens of micrones to a few milimeters. A detail 108 in FIG. 1b shows the entry of coated nanoparticles 105 through the pores of said electrode 101 to said space 104 of the dielectric. Prior to measurement only air or some other gaseous medium is present within said space 104 of the dielectric, in which the quantity of nanoparticles is measured. Said space 104 is defined by a distance between both electrodes 101 and 102. The distance ranges from ten micrometers to several milimeters. The second electrode 102 at the side of the space 104 of the dielectric is insulated by a dielectric 103 impermeable to electricity, fluid, vapour and nanoparticles. Both electrodes 101 and 102 are shown in FIGS. 1a and 1b in the embodiment in the form of parallel flat discs, but the invention also covers other shapes and a different mutual position. Said nanoparticles 105 and the fluid, with which said nanoparticles 105 were coated when flowing through said electrode 101 flow from said space 104 in direction 107.

In an earlier process a fluid, preferably water or butanol is condensed on aerosol nanoparticles 105 by known technological processes, said nanoparticles having a range of size defined by the permeability of known filters or known devices for the separation of particles by size, which filters or devices are located at the entry of the device for counting aerosol nanoparticles. The nanoparticles thus coated change the capacitance of said capacitive sensor upon entering the space 104 of the dielectric of the capacitive sensor. This method allows for detection of said aerosol nanoparticles 105 in a wide scope of their presence in the air, i.e. from one to 30,000 particles per one second and is not specific for any shape or chemical composition of nanoparticles. The method of detection functions independent on the level of humidity of input air containing nanoparticles that are detected. The capacitive sensor used to count nanoparticles has a good self-cleaning capability, since the fluid coating said nanoparticles 105 flows from the side of the capacitive sensor and takes with it a majority of nanoparticles. The capacitive sensor is clean again and prepared for a new measurement. The self-cleaning function extends the operation time of the capacitive sensor and contributes to a less frequent additional cleaning of the capacitive sensor. Low weight of the device of the invention for counting lying below two kilograms and battery supply allow for a construction of a portable detector of aerosol nanoparticles for the use in personal protection.

Entry of coated particles 105 into said space 104 of the dielectric of said capacitive sensor is provided for by a perforation of said electrode 101 as shown in FIGS. 1a and 1b. The second electrode 102 is insulated by an unconductive dielectric 103 and the intermediate space 104 between the dielectric 103 and the perforated electrode 101 is filled with air at the beginning of measurement and is then filled with the fluid used for coating said nanoparticles 105. This fluid increases the capacitance of said sensor capacitor, which can be treated as a flat capacitor in order to understand the process of formation of a signal in first approximation. The capacitance C of the flat capacitor is lineary dependent on the dielectricity factor of the substance c which fills the space between the electrodes of the capacitor by the equation:

$$C = \varepsilon\varepsilon_0 \frac{S}{d}$$

wherein $\varepsilon_0$ is a dielectric constant, S is the surface area of electrodes and d is the distance between the electrodes. The dielectricity factor E and the level of filling of the space between both electrodes 101 and 102 of the capacitor with the substance, like air of fluid brought by coated aerosol nanoparticles 105 are time variable quantities in this case and cause the change in capacitance.

FIGS. 1a and 1b show the following situation: as a new coated nanoparticles 105 enters the space 104 of the dielectric of the sensor capacitor, it causes in the dielectric within the space 104 a local disturbance in the form of a crater encircled by a ring of displaced fluid that increases the level of fluid representing the dielectric in the space 104 above the perforated electrode 101. In the process of local disturbance, the course of which depends on the speed and size of an approaching coated nanoparticle, on the location of approaching, on the depth of the dielectric, on the surface voltage of the dielectric and of the state of the dielectric in the space 104 prior to the approaching with respect to all previous approaches, the crater fills in within several microseconds and the capacitive sensor for counting of nanoparticles is prepared for the approaching of a new coated particle 105. During the process of disturbance, the capacitance of the capacitor, which represents a capacitive sensor, first drops due to the difference in the dielectric constant of water that is ~80 and of the air, which is approximately 1, and then reassumes the original value. The signal, which is measured with the belonging electronics, is first normally positive and, ideally, negative afterwards.

A rapid sequence of approaches of coated aerosol nanoparticles 105 and various locations of approaches, since a particle may approach the centre of the perforated electrode 101, the impermeable part of the electrode 101 and the edge of the electrode 101, can cause also a reverse signal, i.e. first an increase in capacitance and then its decrease and after dying return to the original value.

Figure 1C:
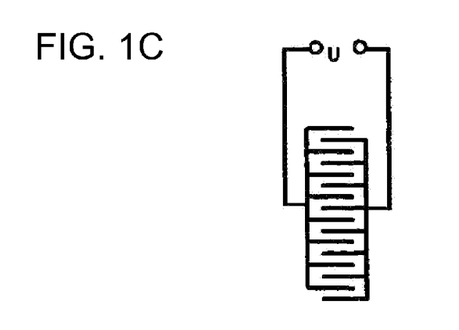

The capacitive sensor may also have a different geometrical constitution, wherein coated nanoparticles may approach the area of the electric field between both electrodes. As shown in FIG. 1c, both electrodes may be designed in the shape of flat metallic rakes inserted one into another. The electrodes can be shaped as a thin layer and applied onto an unconductive material, preferably glass. The capacitive sensor of the invention is two-dimensional. The surface is covered by a fluid brought by coated nanoparticles and covers both electrodes and forms an intermediate dielectric in the mutual electric field. The approach of a fluid coated nanoparticle causes a change in the capacitance of the capacitor for counting nanoparticles.

The rake-shaped electrodes from FIG. 1c can also be three-dimensional. The space between the teeth of the rake serves as a space of the dielectric and nanoparticles enter it between said teeth. The scope of the invention covers any geometry of the electrodes of the capacitive sensor, which allows the entry of aerosol or coated aerosol particles into the space of the dielectric between said electrodes.

The capacitive sensor of the invention may also consist of several capacitors, wherein one electrode may be common.

Figure 6:
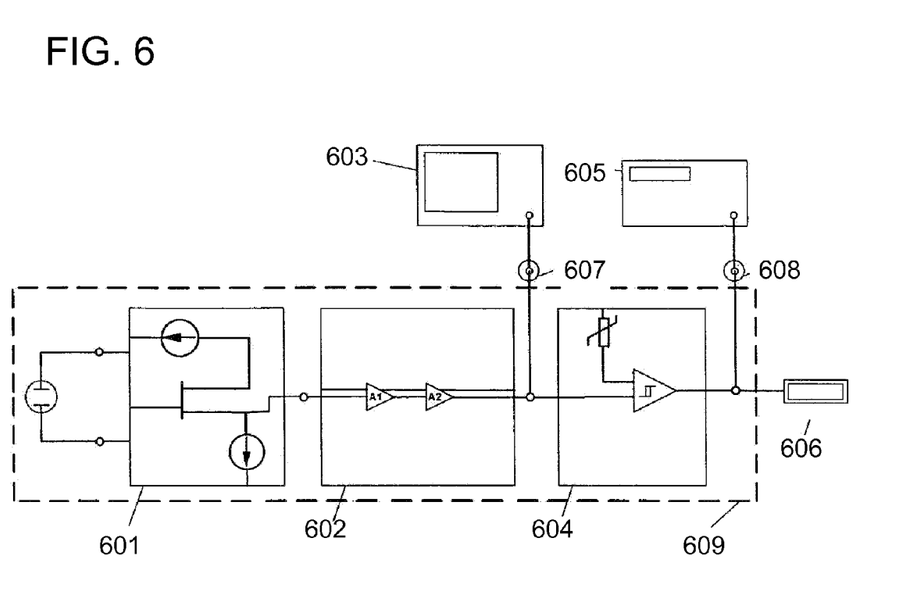
FIG. 6: schematic presentation of the electronics for capturing a signal from the capacitive sensor for counting aerosol nanoparticles.

The electronics for the amplification and evaluation of the signal is schematically shown in FIG. 6. Its functional components are as follows:

If a capacitive sensor 309 for counting nanoparticles is connected, a preamplifier 601 provides for a transformation of a dynamic component of a change in capacitance into an analogous electric signal. Said preamplifier 601 functions as a voltage follower on the capacitor for counting nanoparticles and maintains constant static voltage, excluding the latter from the signal. If a coated nanoparticle 105 approaches, a pulse with greatest response up to 100 µV appears on the capacitive sensor 309 and consequently also at the output of the preamplifier 601. The pulse may be of various lengths and shapes. A typical pulse length is several 10 µs and the frequency field of the preamplifier 601 is 1 kHz to 10 MHz. The electronic for the amplification and evaluation of the signal is protected by an EMI shield 609 due to possible influences from the environment.

Two-stage amplifier 602 that amplifies a voltage signal on each of the stages by the factor 10.

The output signal is thus amplified by the factor 100, which means the greatest response to 10 mV and is led to standard electronic measuring devices that allow the monitoring of the signal.

Device for monitoring a signal, for instance an oscilloscope 603 that is connected to the output of the analogue signal 607.

To provide for the response count the signal may be led to numerous devices capable of capturing a specific response, e.g. with analogue filters and also in combination with an analogue comparator 604 or a digitally programmed analyser 605 to recognise patterns of the signal, which is connected to the output of the digital signal 608. Digitally processed signals are led to the count display or to a more powerful computer system that enables advanced display, archiving of measurements and link to other devices.

Embodiment

Figure 2A:
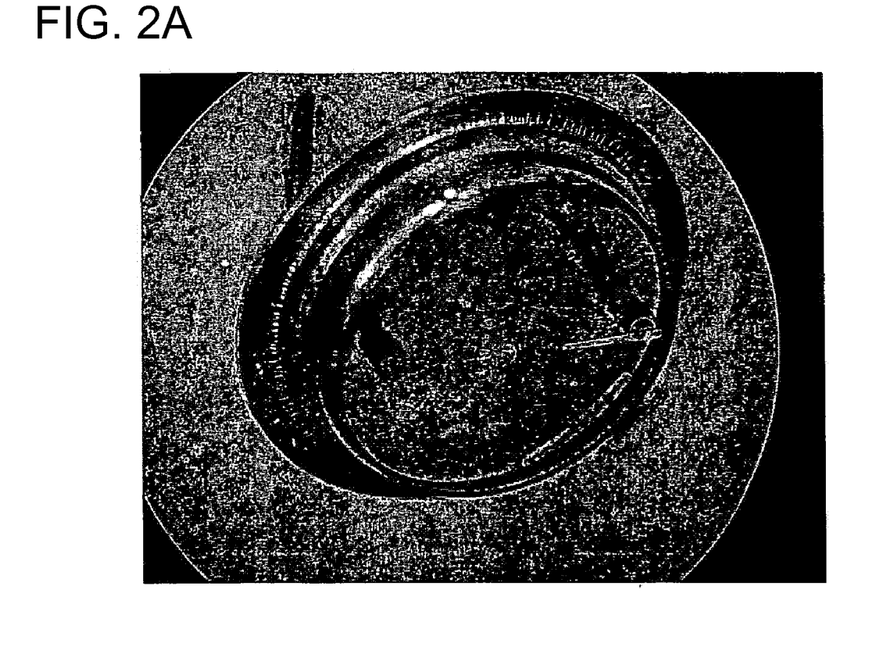
Figure 2B:
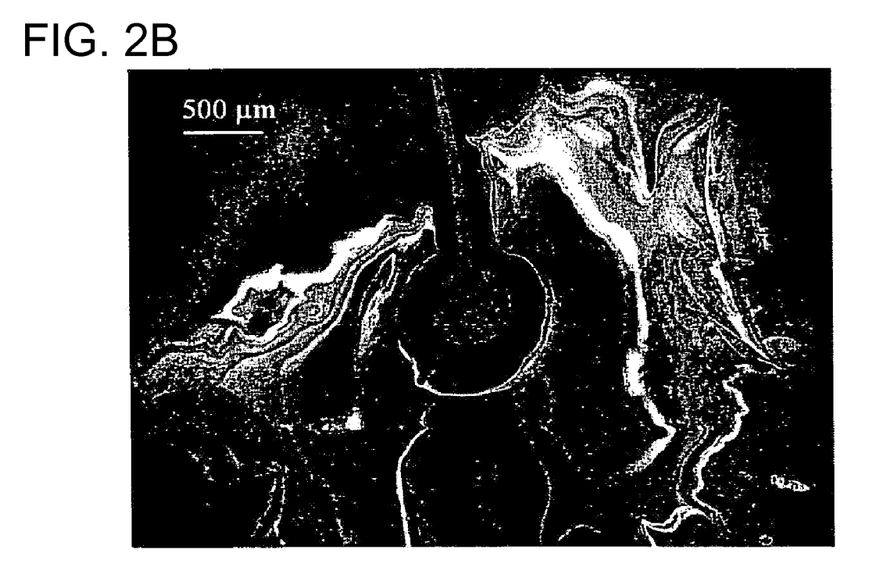

The embodiment of a method for counting nanoparticles is represented by a capacitive sensor as shown in FIGS. 1a and 1B. The capacitive sensor consists of two electrodes, of which the first electrode 101 if contemplated from the direction of approaching of coated nanoparticles 105 is formed as a metallic mesh 101, and the second electrode 102 is vapour phase deposited onto ground glass of a round support having a diameter of 5 mm with built-in electric ducts. A thin layer of the dielectric 103 is put onto the second electrode 102, for instance Kapton having a thickness of 12 micrometers. The first electrode 101 is a standard microscopic mesh produced from copper with a thickness of 15 µm, the side of square windows measures 85 µm and the width of the crossbar is 40 µm. The second electrode 102 is of gold in the shape of a circle having a diameter 0.4 mm as shown in FIGS. 2a, b. The gold is vapour deposited onto polished glass, or the electrode may be cut into the previously vapour deposited gold layer by use of laser ablation. The distance between the first electrode 101 and the second electrode 102 of the capacitive sensor is 50-100 µm. The intermediate space between both electrodes 101 and 102 is empty with the exception of a thin layer of the insulation dielectric 103 as in FIG. 1b and is then filled by a fluid brought about by the coated nanoparticles 105 as shown in FIG. 1b.

As depicted in FIG. 3 the device for counting aerosol nanoparticles consists of water reservoir 301, heater 302, vapouriser 303, water vapour jet 304, pores 305 for the supply of air with nanoparticles, water vapour area 306, condensation chamber 307, wherein water from water vapour 304 is condensed on nanoparticles, temperature meter 308 for temperature control within said condensation chamber 307, capacitive sensor 309, exhaust pipe 310 and electronic 311 for the measurement and amplification of the signal of said capacitive sensor 309.

As shown in FIGS. 1a, b the nanoparticles 105, on which water had condensed in an earlier process (which is not part of the present invention) and had grown up to a size of several micrometers, approach with a speed of some 25 m/s to the first electrode 101 having the shape of a metallic mesh. The electronic 311 from FIG. 3 for the detection of changes in capacitance maintains the voltage 500 mV on the capacitive sensor 309 that dynamically changes very slowly. The approach of nanoparticles 105 that changes the capacitance causes a slight oscillation of this voltage, since the charge of the capacitor remains unchanged.

At the beginning of measurement, the space between both electrodes 101 and 102 of the capacitive sensor from FIGS. 1a, b first fills with water brought about by coated nanoparticles 105. The water 104 from FIG. 1b represents an additional dielectric of the capacitive sensor. The speed of approach of coated nanoparticles 105 is gained by regulated pumping of the flow of air with nanoparticles. Coated nanoparticles 105 having the shape of drops with a diameter of a few micrometers approach the first electrode 101 having the form of a metallic mesh from FIG. 1b. As a nanoparticle-containing drop hits the dielectric 104 in the mesh window, it causes a crater in the water and the displaced water collects on the edge above the original water level.

Figure 4:
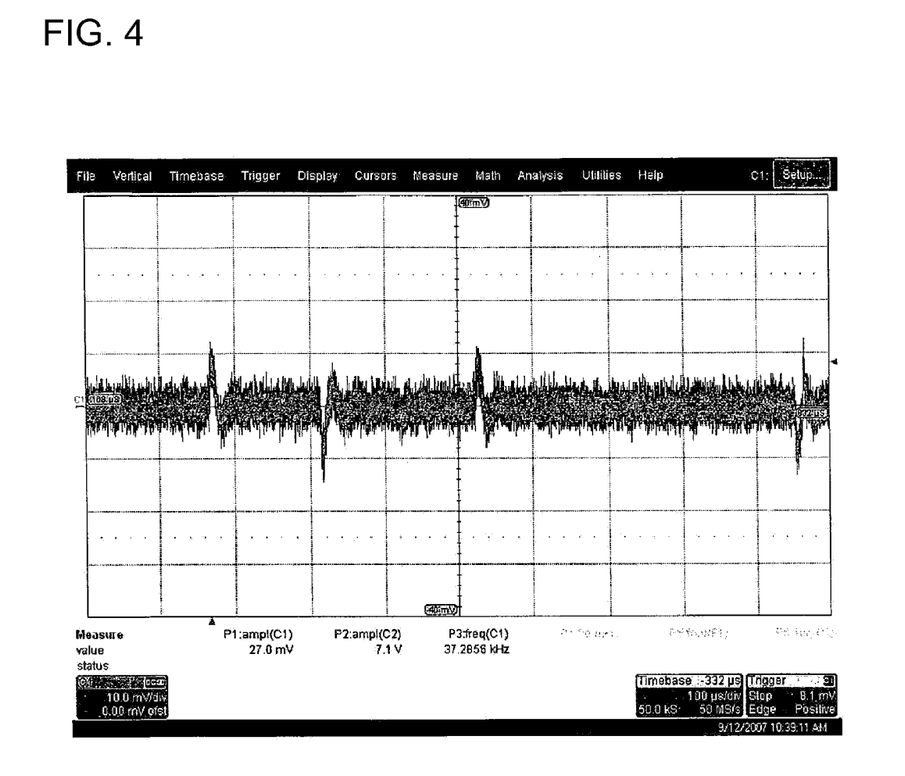
FIG. 4: signals on the oscilloscope (Lecroy Waverunner 6030) that appeared during detection of coated nanoparaticles with the capacitive sensor.
Figure 5:
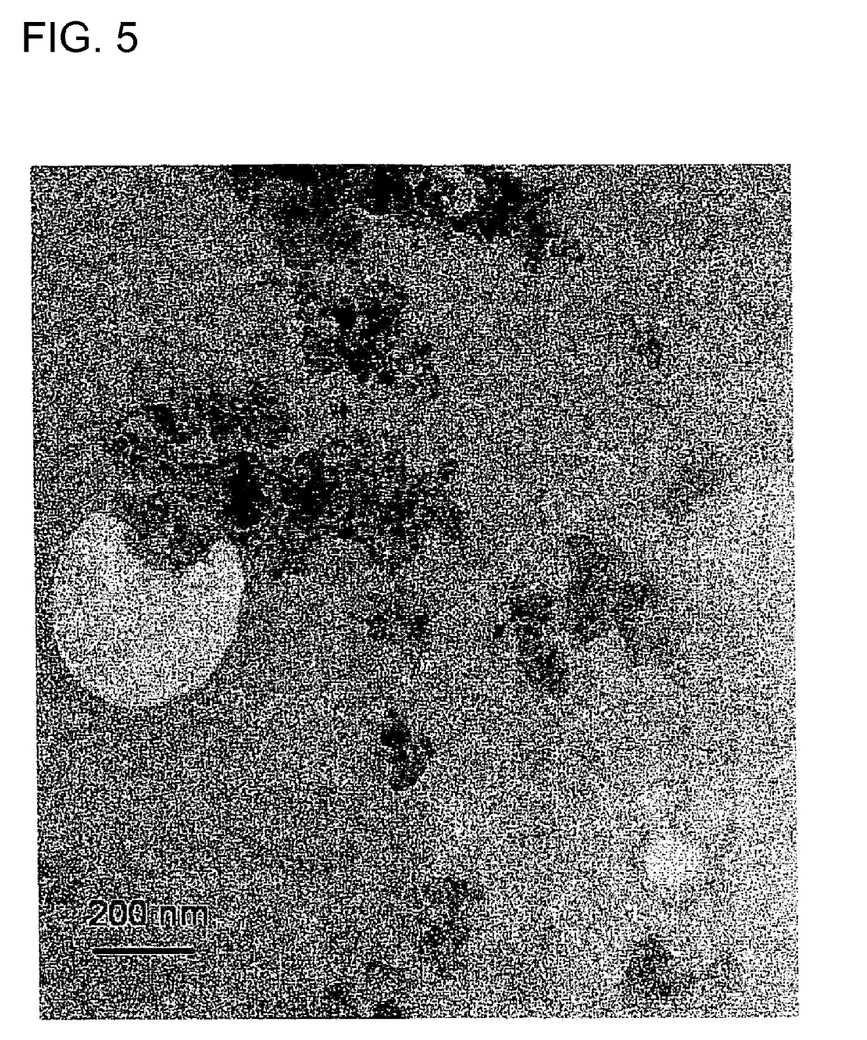
FIG. 5: image of nanoparticles at the output of the capacitive sensor taken with a translucent electronic microscope to field emission Jeol 2010 F.

Part of the water is displaced from the interior of the capacitive sensor for a short period of time. The static capacitance of the sensor capacitor for the counting of nanoparticles and having a 12 μm thick layer of kaptor is several pF. As a water-coated particle approaches, a change in the capacitive sensor occurs and causes the change in capacitance less than 0.1%, which is enough for detection. The signal amplitude thus only amounts to a few microvolts as shown in FIG. 4 and changes as a function of the spot of approach of the coated nanoparticle 105. The excess water drains from the capacitive sensor 309 for counting nanoparticles and mostly takes with it the nanoparticles shown in FIG. 5 and thus provides for immediate cleaning of the capacitive sensor 309.

The electronic for signal amplification and evaluation is schematically shown in FIG. 6. Its functional components are as follows:

The preamplifier 601 connected to the capacitive sensor 309 for the counting of nanoparticles allows the transformation of the dynamic component of the change in capacitance into an analogue electric signal.

The preamplifier 601 disposes over the following functions: a) low-noise voltage regulator for static supply of the capacitor for the counting of nanoparticles, work voltage approximately 500 mV, b) low-noise amplifier with a high-ohmic input. The preamplifier 601 does not amplify the voltage of the signal but functions as a voltage follower on the capacitor for the counting of nanoparticles, moreover, it maintains the constant static voltage (and excludes the latter from the signal). As the coated nanoparticle 105 approaches, a pulse appears on the capacitive sensor 309 and consequently also on the output of the preamplifier 601, said pulse having the highest response up to 100 μV. The pulse may be of various length and shape. The typical length of the pulse is several 10 μs, the frequency field of the preamplifer 601 ranges from 1 kHz to 10 MHz. Apart from the dynamical component of the capacitance of the capacitive sensor for the counting of nanoparticles, the so-called stray capacitance on the input of the preamplifier 601 has influence on the size and shape. The obtained output signal thus has other components having influence on response. Apart from the stray capacitance other environmental electromagnetic disturbances, especially internal noise, have influence on the response. It is required that the sum of all unwanted elements causing response is less than the dynamic change in the capacitive sensor 309 for the counting of nanoparticles, which represents a useful response. The signal amplification and evaluation electronic is protected by the EMI shield 609 due to possible influences from the environment.

Two-stage amplifier 602, which amplifies the voltage signal on each level by the factor 10.

The output signal thus amplifies by the factor 100, which means the largest response to 10 mV and is led to standard electronic measuring devices that allow to monitor the signal.

Signal monitoring device, for instance the oscilloscope 603 that is connected to the output of the analogue signal 607.

In order to count responses, the signal may be led to numerous devices capable of capturing a specific response, e.g. with analogue filters, or also in combination with an analogue comparator 604 or a digitally programmed analyser for detecting patterns of the signal 605 connected to the output 608 of the digital signal. Digitally processed signals are led to the count display 606 or to a more powerful computer system that enables advanced display, archiving of measurements and link to other devices.

The invention claimed is:

1. A method of increasing a sensitivity of counting aerosol nanoparticles comprising:
   (a) changing a capacitance of a capacitor by impacting a gas comprising fluid coated nanoparticles to at least a portion of a dielectric space defined between a first perforated mesh electrode and a second insulated electrode covered with an unconductive dielectric layer of the capacitor being filled with water, wherein said impacting of said fluid coated nanoparticle in the dielectric space temporarily creates a crater defined by said fluid coated nanoparticle protruding into said dielectric space;
   (b) measuring the pulse capacitance in microsecond time scale when said fluid coated nanoparticles impact said dielectric space between said first electrode and said second electrode; and
   (c) determining a number of changes in pulse capacitance from said number of nanoparticles per volume unit of gas in microsecond time scale entering said dielectric space, wherein said changes of pulse capacitance indicates the number of nanoparticles in a microsecond time scale.

2. A capacitor comprising:
   (a) a first perforated electrode, wherein said perforated electrode consists of a mesh;
   (b) a second insulated electrode, wherein said insulated electrode being covered with an unconductive dielectric layer impermeable to electricity, fluid, vapor, and nanoparticles; and
   (c) a dielectric comprising a space defined between the first electrode and the second electrode and being filled with water,
   wherein the capacitor is configured such that impacting the dielectric space with a gas comprising fluid coated nanoparticles temporarily causes craters defined by said fluid coated nanoparticles protruding into said dielectric space, and said craters cause said capacitor to exhibit a change in pulse capacitance such that the number of changes in pulse capacitance indicates the number of nanoparticles in a microsecond time scale.

3. The capacitor according to claim 2, wherein the space of the dielectric comprises a two-dimensional space or a three-dimensional space.

4. The capacitor according to claim 2, wherein one of the first electrode, second electrode, or first and the second electrodes comprise a plurality of portions.

5. A detector for increasing sensitivity of measuring nanoparticles in a gas, the detector comprising at least one capacitor comprising:
   (a) a first perforated electrode, wherein said perforated electrode consists of a mesh;
   (b) a second insulated electrode, wherein said insulated electrode being covered with an unconductive dielectric layer impermeable to electricity, fluid, vapor, and nanoparticles; and
   (c) a dielectric comprising a space defined between the first electrode and a second electrode, said space being filled with water,
   wherein the at least one capacitor is configured such that said at least one capacitor exhibits a change in pulse capacitance upon impacting fluid coated nanoparticles to at least a portion of the dielectric space, such that a crater is temporarily created by the fluid coated nanoparticle protruding into said dielectric space, to enable separation between single impacts of fluid coated nanoparticles for counting a number of nanoparticles in a microsecond time scale.

\* \* \* \* \*